US012714313B2

(12) United States Patent
Eschenburg et al.

(10) Patent No.: US 12,714,313 B2
(45) Date of Patent: Aug. 25, 2026

(54) SENSOR LAYER FOR DETERMINING TEMPERATURE PROFILES ON A SKIN SURFACE, AID FOR APPLICATION TO A SKIN SURFACE, METHOD FOR PRODUCING AN AID, AND METHOD FOR DETERMINING A RELATIVE TEMPERATURE DIFFERENCE ON A SKIN SURFACE

(71) Applicant: ORTHOPAEDIE-TECHNIK-SERVICE AKTIV GMBH, Greifswald (DE)

(72) Inventors: Christian Eschenburg, Greifswald (DE); Alf-Matthes Scheibeler, Holldorf (DE); Frank Starkowski, Lubmin (DE); Guenther Tausch, Datzetal (DE)

(73) Assignee: ORTHOPAEDIE-TECHNIK-SERVICE AKTIV GMBH, Greifswald (DE)

( * ) Notice: Subject to any disclaimer, the term of this patent is extended or adjusted under 35 U.S.C. 154(b) by 1311 days.

(21) Appl. No.: 17/613,094

(22) PCT Filed: May 22, 2020

(86) PCT No.: PCT/DE2020/200037

§ 371 (c)(1),
(2) Date: Nov. 22, 2021

(87) PCT Pub. No.: WO2020/233756

PCT Pub. Date: Nov. 26, 2020

(65) Prior Publication Data

US 2022/0313096 A1 Oct. 6, 2022

(30) Foreign Application Priority Data

May 23, 2019 (DE) ..................... 10 2019 113 719.5
Aug. 14, 2019 (DE) ..................... 10 2019 121 927.2

(51) Int. Cl.
*A61B 5/01* (2006.01)
*A61B 5/00* (2006.01)

(52) U.S. Cl.
CPC .............. *A61B 5/01* (2013.01); *A61B 5/0008* (2013.01); *A61B 5/6801* (2013.01); *A61B 2562/0271* (2013.01); *A61B 2562/04* (2013.01)

(58) Field of Classification Search
CPC ....... A61B 5/01; A61B 5/0008; A61B 5/6801; A61B 2562/0271; A61B 2562/04;
(Continued)

(56) References Cited

U.S. PATENT DOCUMENTS 10,080,524 B1 9/2018 Xi
2005/0245839 A1 11/2005 Stivoric et al.
(Continued)

FOREIGN PATENT DOCUMENTS

CN 103385699 A 11/2013
JP 5051767 B2 10/2012
(Continued)

*Primary Examiner* — Abid A Mustansir
(74) *Attorney, Agent, or Firm* — Norman B. Thot

(57) ABSTRACT

A sensor layer for determining temperature profiles on a skin surface. The sensor layer includes at least one ply, a contact layer with the skin surface, the contact layer being arranged on a top side of the at least one ply, a plurality of temperature sensors arranged at least one of in the at least one ply and on the top side of the at least one ply, and conductor tracks arranged at least one of in the at least one ply and on the top side of the at least one ply. The conductor tracks are electrically connected to the plurality of temperature sensors so that the sensor layer is formed to be flexible and so that a temperature difference on the skin surface can be determined via the contact layer.

14 Claims, 1 Drawing Sheet

(58) Field of Classification Search
CPC ... A61B 5/6807; A61B 5/6811; A61B 5/6828; A61B 5/6831; A61B 5/6892; A61B 5/6894; A61B 2562/12; A61B 2562/164; A61B 2562/227; A61B 5/445; A61B 5/015; A61B 5/6802; A61B 5/6891; A61B 5/746; A43B 3/34; A43B 13/023; A43B 13/00; A43B 17/00
See application file for complete search history.

(56) References Cited

U.S. PATENT DOCUMENTS

| | | | |
|---|---|---|---|
| 2006/0047218 A1 | 3/2006 | Bloom et al. | |
| 2011/0264001 A1 | 10/2011 | Cheung et al. | |
| 2017/0007133 A1 | 1/2017 | Mei et al. | |
| 2018/0028071 A1* | 2/2018 | Shi | A61B 5/282 |
| 2018/0028072 A1* | 2/2018 | Shi | A61B 5/6833 |
| 2018/0184908 A1 | 7/2018 | Meyerson et al. | |
| 2018/0256100 A1 | 9/2018 | Li | |
| 2020/0261629 A1 | 8/2020 | Hunt et al. | |

FOREIGN PATENT DOCUMENTS

| | | |
|---|---|---|
| RU | 2 677 061 C1 | 1/2019 |
| WO | WO 2019/063488 A2 | 4/2019 |

* cited by examiner

SENSOR LAYER FOR DETERMINING TEMPERATURE PROFILES ON A SKIN SURFACE, AID FOR APPLICATION TO A SKIN SURFACE, METHOD FOR PRODUCING AN AID, AND METHOD FOR DETERMINING A RELATIVE TEMPERATURE DIFFERENCE ON A SKIN SURFACE

CROSS REFERENCE TO PRIOR APPLICATIONS

This application is a U.S. National Phase application under 35 U.S.C. § 371 of International Application No. PCT/DE2020/200037, filed on May 22, 2020 and which claims benefit to German Patent Application No. 10 2019 113 719.5, filed on May 23, 2019, and to German Patent Application No. 10 2019 121 927.2, filed on Aug. 14, 2019. The International Application was published in German on Nov. 26, 2020 as WO 2020/233756 A1 under PCT Article 21(2).

FIELD

The present invention relates to a sensor layer for determining temperature profiles on a skin surface, the sensor layer having a contact layer with the skin surface, wherein the sensor layer has at least one ply (105) and the contact layer is arranged on a top side of the at least one ply. The present invention also relates to an aid for application to a skin surface, a method for producing an aid, and to a method for determining a relative temperature difference on a skin surface.

A deep tissue defect (ulcer) and a superficial tissue defect (wound) of the skin are generally perceived only when the skin reddens as a result of inflammation. Inflammation is often perceived too late, in particular in patients who are at risk, for example, who are diabetic or bedridden, resulting in the formation of a wound that is difficult to treat, in tissue damage and/or even in amputation.

In the case of skin that is susceptible to tissue defects, as is the case for diabetics or people who are bedridden, there is the additional problem that the skin is already susceptible to irritation and/or pressure. For this reason, rigid measuring sensors and/or the associated measuring sensor systems cannot be brought into direct contact with the skin surface, which is already susceptible as it is. It is furthermore often necessary to monitor areas of the body that are already exposed to a pressure load as a result of the body weight, such as, for example, the soles of the feet or the back in the case of a bedridden patient.

A resistive temperature sensor array is described in CN 103385699 A in which temperature-sensitive films are arranged on a flexible substrate film, and the flexible substrate film is fixed on a solid substrate, such as a printed circuit board or glass plate. While the flexible substrate film can be applied to a skin surface, pressure points occur on the skin surface as a result of the solid substrate in the event of loading or movement.

Application of pressure to a skin surface is likewise disadvantageous in the case of a three-dimensional electronic compress described in US 2017/0007133 A1 and a wearable compress described in US 2018/0184908 A1 with two temperature sensors arranged in materials with different material thicknesses.

A system for monitoring a patient's body temperature is also described in US 2011/0264001 A1 in which a curved temperature sensor can be secured and stuck on the skin of a patient via a releasable security strip.

SUMMARY

An aspect of the present invention is to improve upon the prior art.

In an embodiment, the present invention provides a sensor layer for determining temperature profiles on a skin surface. The sensor layer includes at least one ply, a contact layer with the skin surface, the contact layer being arranged on a top side of the at least one ply, a plurality of temperature sensors arranged at least one of in the at least one ply and on the top side of the at least one ply, and conductor tracks arranged at least one of in the at least one ply and on the top side of the at least one ply. The conductor tracks are electrically connected to the plurality of temperature sensors so that the sensor layer is formed to be flexible and so that a temperature difference on the skin surface can be determined via the contact layer.

BRIEF DESCRIPTION OF THE DRAWINGS

The present invention is described in greater detail below on the basis of embodiments and of the drawings in which.

DETAILED DESCRIPTION

Figure 1:
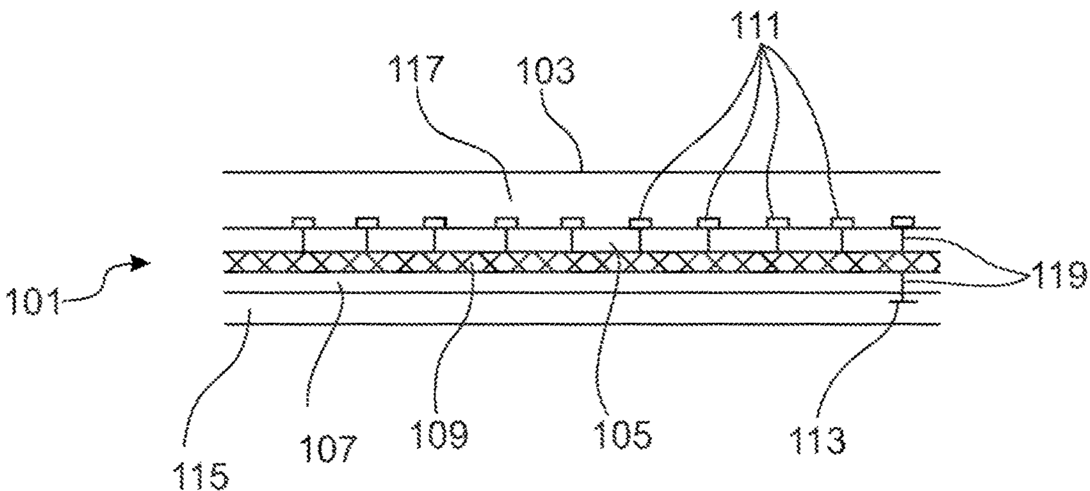
FIG. 1 shows a highly schematic sectional illustration, which is not to scale, of a sensor layer with a connected aid preform and a cushion layer.
Figure 2:
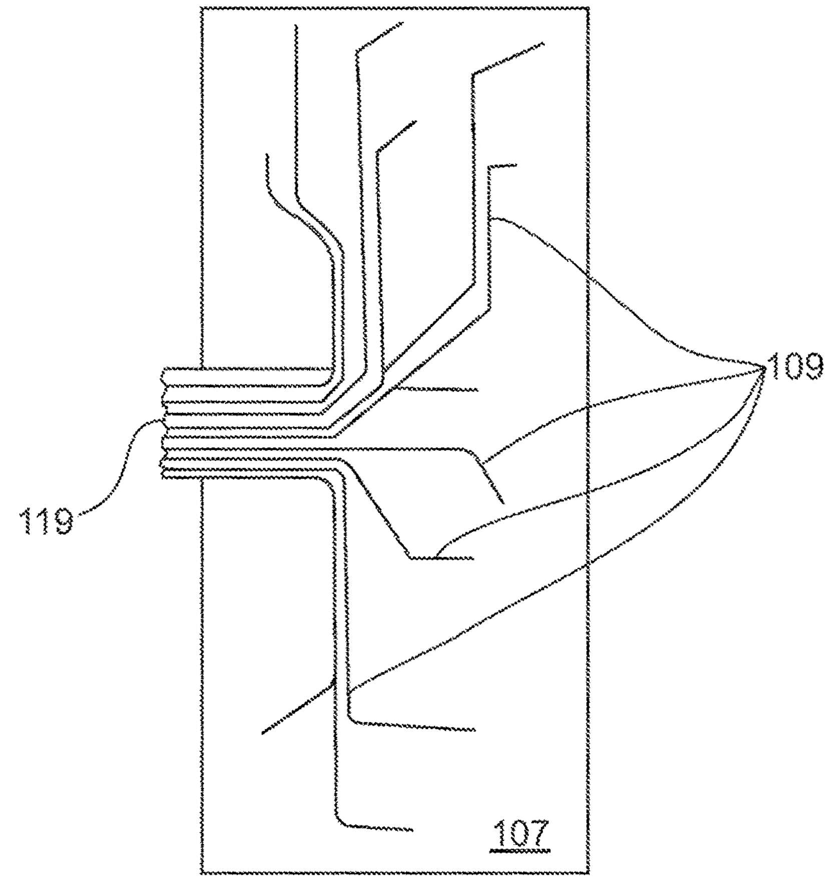
FIG. 2 shows a highly schematic top view of a PU bottom ply of the sensor layer with conductor tracks.

The present invention provides a sensor layer for determining temperature profiles on a skin surface, the sensor layer having a contact layer with the skin surface, wherein the sensor layer has at least one ply and the contact layer is arranged on a top side of the at least one ply, wherein conductor tracks are arranged on the top side of the at least one ply and/or in the at least one ply, the conductor tracks being electrically connected to a plurality of temperature sensors in the at least one ply and/or on the top side of the at least one ply so that the sensor layer is formed to be flexible and a temperature difference on the skin surface can be determined via the contact layer.

A flexible sensor layer is thereby provided for identifying and observing temperature differences on the skin and thus for the early identification of inflammations by monitoring a skin surface or a plurality of skin surfaces and/or skin regions. A negative temperature difference determined at the position of the corresponding temperature sensor indicates, for example, a poor blood circulation in the corresponding skin area. A positive temperature difference in one temperature sensor compared to the other temperature sensors indicates a local temperature increase and thus incipient inflammation. Developing inflammation on, beneath and/or in the skin is consequently identifiable at an early stage and can subsequently be treated in a timely manner without the occurrence of sequelae. This makes it possible to prevent inflammations, ulcers and amputations via high-resolution monitoring of the skin temperature over a skin surface and/or as the difference between two or more skin surfaces.

The flexible sensor layer serves to measure temperature continuously or discontinuously and thus to monitor over time the temperature of a person with a known, already diagnosed illness, or a person at risk, as an indicator and thus as a sign of a possible illness. A temperature increase can, for example, indicate inflammation. It is up to a doctor to interpret this as a morbid condition and/or to establish the nature of the inflammation-inducing illness; this does not fall within the direct use of the flexible sensor layer.

A key concept of the present invention lies in the fact that the sensor layer is formed so that it can be optimally fitted to a skin surface in a flexible, three-dimensional manner, and all of the adjacent skin surface is monitored by the temperature sensors even if the skin area moves, without pressure being applied to the skin surface by the conductor tracks and/or the temperature sensors. The conductor tracks, which are in particular flexible, and the temperature sensors are here embedded on and/or in the at least one ply of the sensor layer so that they do not apply any increased pressure or any other type of irritation to the skin surface via the contact layer. It is particularly advantageous that the entire sensor layer, including the conductor tracks, is formed to be flexible, and not just the contact layer.

The functional sensor layer is in particular set up to allow temperature differences to be measured and identified in order to detect an inflammation. Measurement of absolute temperature values is here not necessary.

The measuring of temperature differences close to the body is accomplished through at least one layer. It is in this case the contact layer of the sensor layer, and/or through an additional textile layer, such as a garment, that surrounds the skin surface. The contact layer thus makes contact with the skin surface directly or indirectly via the piece of fabric worn against the skin.

It is here particularly advantageous that the sensor layer with the temperature sensors has a thickness ranging from 0.5 mm to 2.5 mm, for example, from 1.0 mm to 2.0 mm.

This provides good heat transfer between the contact layer and the temperature sensors and avoids pressure stimuli from the conductor tracks and/or temperature sensors.

The following terminological explanations should be provided:

A "sensor layer" is in particular a three-dimensional body which is delimited by two surfaces as the top and bottom sides of the layer, which has a layer thickness lower than the extension of the surfaces of the top and bottom sides of the layer, and which has one or more measuring sensors. The sensor layer in particular has one or more layers and/or one or more plies. The sensor layer in particular has a contact layer on its top layer surface and/or an aid on its bottom layer surface. The sensor layer is in particular flexible and/or extensible.

A "temperature profile" is understood to in particular mean a variation of the temperature along and/or over a skin surface and/or over time at the same temperature sensor or sensors and/or at the same allocated skin position or positions. A temperature profile is thus understood to mean a spatial and/or temporal temperature profile. The temperature profile of the corresponding skin surface can be visualized online, for example, using a smartphone app.

A "skin surface" is in particular the surface of skin that covers a body and/or a body part. The skin surface is in particular the surface of the outermost layer (upper skin, epidermis) of the skin.

A "contact layer" (also called a "cushion layer") is in particular a layer of material with a thin layer thickness and a two-dimensional extension in which one surface side is in direct and/or indirect contact with the skin surface. The contact layer in particular makes contact with the skin surface via its layer top side. A "cushion layer" in particular comprises a material that effects mechanical damping, size compensation, surface fitting and/or embedding and/or support of the limb to which the skin surface belongs. A cushion layer in particular comprises elastic resilience, insulation and/or padding. Natural or synthetically produced substances, such as, for example, plant or animal fibers or synthetically produced foams and foamed nonwovens as well as other plastics and polymers, can in particular be used as the cushion layer.

It is particularly advantageous that the contact layer, which is in direct or indirect contact with the skin surface, is thermally insulating and/or heat insulating. The thermally insulating properties of the contact layer provide that a brief local temperature increase on the skin surface is attenuated and thus a misinterpretation of the temperature data is avoided. Since inflammations are known to form relatively slowly, unsound measures and unnecessary treatments are thereby prevented. A "steady state" measurement thus takes place.

A "ply" is understood to in particular mean a layer of a single sheet. A ply can in particular comprise paper, card, foil, plastic and/or textile material. The "bottom ply" of the sensor layer is the one that is arranged on the bottom side of the sensor layer and/or is in contact with the aid. The "top ply" of the sensor layer is the ply on which the temperature sensors and the contact layer are arranged.

A "temperature sensor" is in particular an electrical or electronic component which provides an electrical signal as a measure of a temperature and/or temperature distribution.

A temperature sensor is in particular a thermistor, such as, for example, an NTC thermistor (negative temperature coefficient thermistor) which has a negative temperature coefficient and conducts electrical current better at high temperatures than at low temperatures. The temperature sensor can also be a PTC thermistor (positive temperature coefficient thermistor) which has a positive temperature coefficient and which conducts electrical current better at low temperatures than at high temperatures. Each temperature sensor on the surface of and/or in the at least one ply of the sensor layer is connected between two conductor tracks in each case. The temperature sensor is bonded for this purpose, for example, to the contact surface, for example, to the gold contact surface, of each conductor track by gluing or soldering. It is particularly advantageous if each temperature sensor is embedded in the at least one ply and has its top side in contact with the bottom side of the contact layer. The temperature sensors can, however, also be covered with a thin ply, for example, a thin polyurethane layer, and can be in contact with the contact layer via this thin ply.

A "temperature difference" is in particular the difference in the temperatures of two or more temperature measuring points and/or temperature sensors. A temperature difference of a temperature sensor or of multiple temperature sensors relative to the other temperature sensors of the sensor layer can in particular indicate an inflammation or other type of defect in the skin.

A "conductor track" is in particular an electrically conductive connection with a "two-dimensional" routing. The conductor track in particular extends in one plane (conductor track plane) and in particular serves to supply current and/or power, transmit signals and/or dissipate heat. The conductor tracks can also be arranged in a plurality of conductor track planes with electrically insulating planes arranged therebetween, in which case, for example, a connection between the individual conductor track planes is achieved via vertical, electrically conductive connections. A conductor track in particular comprises an electrically conductive material, for example, copper and/or a copper alloy. The conductor tracks can also be formed by a conductive paste, in particular a silver conductive paste, in which case the silver conductive paste is arranged on the top side of the at least one ply and/or in the at least one ply. The conductive paste can, for example, be sandwiched between the bottom ply and the top ply. It is particularly advantageous for the conductor tracks to be formed by conductive paste because silver conductive paste is in particular unaffected by expanding, bending, stretching and/or folding.

In an embodiment of the sensor layer, the sensor layer can, for example, have a bottom ply and a top ply and the contact layer is arranged on the top ply, wherein conductor tracks are arranged between the bottom ply and the top ply, the conductor tracks being electrically connected to a plurality of temperature sensors in the top ply and/or on a top side of the top ply.

Because the conductor tracks and/or temperature sensors are embedded between the bottom ply and the top ply of the sensor layer, the conductor tracks and/or temperature sensors can be inserted in a simple manner between the top side of the bottom ply and the bottom side of the top ply. The conductor tracks and/or temperature sensors are also optimally embedded between the two plies so that they do not apply any increased pressure or other type of irritation to the skin surface via the contact layer.

In an embodiment of the sensor layer, the conductor tracks can, for example, be formed to be evenly spaced, meandering and/or vein-like.

An even spacing of the conductor tracks, for example, by configuring them in parallel or as a network of squares, allows them to be optimally configured coextensively with a layer arranged thereon or thereunder.

It is particularly advantageous if the conductor tracks are formed to be vein-like and/or meandering since this further improves the flexibility of the sensor layer. The conductor tracks are thus formed so as to be dynamically movable. A breakage of the conductor tracks, and thus of the electrical connections, due to extension, bending, stretching and/or folding of the sensor layer is consequently prevented, an optimum fitting to the skin surface is allowed, and a pressure load on the skin is avoided. For this purpose, the conductor tracks are in particular technically formed so that the conductor tracks can withstand dynamic forces, such as extension and compression, over a prolonged period, in particular at least during the measuring period.

The meandering and/or vein-like conductor tracks can, for example, extend in the horizontal plane in a finger-like manner from an electronic circuit, in particular a PCB, into the periphery as far as the temperature sensors. Increased flexibility is thereby achieved, and consequently a better three-dimensional fitting to a desired shape, such as, for example, to an aid or a carrier of the sensor layer.

"Meandering" is understood to in particular mean a path in the form of successive loops, twists and/or curves.

"Vein-like" is understood to in particular mean that the conductor tracks have a shape like branching veins.

In order to make the sensor layer flexible and/or extensible, the sensor layer comprises a flexible plastic, in particular polyurethane.

It is particularly advantageous that the sensor layer is configured to be flexible on the basis of its material, in particular flexible polyurethane (PU) or another flexible plastic, and/or on the basis of the embedded dynamic conductor tracks between the bottom ply and the top ply. The sensor layer can thus exhibit extensibility of up to 30% of its dimension in the unstressed state.

It is particularly advantageous that the sensor layer comprises a crosslinkable plastic so that the flexibility of the plastic can be adjusted to suit requirements. The properties of polyurethane can, for example, be varied over a broad range via the degree of crosslinking and/or the constituents employed (in particular isocyanate or OH constituents) so that thermosets, thermoplastics or elastomers are present.

"Polyurethane" is in particular a plastic or synthetic resin obtained from the polyaddition reaction of dialcohols and/or polyols with polyisocyanates. Polyurethane can in particular be present as a flexible or rigid foam or as a textile elastic fiber material.

In a further embodiment of the sensor layer, each temperature sensor can, for example, have a maximum dimension of ≤2 mm, in particular ≤1.8 mm, for example, ≤1.5 mm.

Because of the low height, width and length of each temperature sensor, each temperature sensor occupies only a very small space on the top side of the top ply and, because of the contact layer (cushion layer) arranged thereover, it does not lead to a pressure load on the skin surface.

In order to measure all the relevant skin surface, each temperature sensor has a measuring radius ranging from 2.5 cm to 1.5 cm, for example, from 2.3 cm to 1.7 cm.

The temperature sensors can, for example, be arranged evenly over the surface of the top ply of the sensor layer and/or so as to cover the entire area so that, because of the measuring radii of the temperature sensors, the entire skin surface that is in contact with the contact layer is sensed and/or measured. The measuring radius of each temperature sensor is additionally designed to be so sensitive that it can even penetrate a plurality of layers (such as textile layers).

A "measuring radius" is understood to in particular mean a distance between the center point of a temperature sensor and a circular line arranged around it, within which the temperature sensor measures a temperature. The measuring radius in particular ends at the spherical outer surface of a three-dimensional sphere around the center point of the measuring sensor.

To avoid a misinterpretation of the temperature data in the event of a brief local temperature increase, the contact layer is thermally insulating so that a brief temperature increase on the skin surface is determined in an attenuated manner.

Because a determined temperature increase is attenuated via the contact layer, a corresponding temperature difference of the skin is not immediately interpreted as exceeding a predefined threshold value, and a false alarm and unnecessary treatment steps are thus avoided.

"Thermally insulating" is understood to in particular mean that the contact layer has a material property so that the passage of heat or cold through the contact layer is reduced. The temperature at the skin surface is as a result detected at the temperature sensors that are arranged under the contact layer in particular in an attenuated manner through the contact layer.

To serve as a carrier for the sensor layer and to fit it optimally to the skin surface, the sensor layer is connected to an aid via a bottom side of the at least one ply or of the bottom ply.

On the one hand, the aid serves to fix the sensor layer on the body, in particular via a form-fitting connection. The aid, and thus the sensor layer, thus fit closely and three-dimensionally to the shape of the region of the body to be measured owing to their elasticities and/or the cut. This provides that, even if the aid is put on again, reapplied and/or reused, each temperature sensor sits repeatably at its predefined position relative to the skin surface.

An "aid" is in particular arranged on the bottom side of the bottom ply of the sensor layer. An aid is, for example, an insole, bandage, seat surface of a wheelchair, sheet for a care bed, liner in a prosthetic socket or a similar object, which comes into direct or indirect contact with a skin surface. As well as a bandage, in which a movement of the bandaged body part is possible, an aid can also be an orthosis for immobilizing the body part. An aid is not, of course, limited to medical uses. An aid is in particular also any type of functional object that can come into contact with the surface of a body. An aid is, for example, also an insole in a sports shoe or a strap for a fitness wristband.

In a further embodiment of the sensor layer, the conductor tracks can, for example, be electrically connected to an electronic circuit, in particular to a PCB, in and/or on the aid.

The aid thus also acts at the same time as a mount for a temperature sensor system assigned to the sensor layer, in particular an electronic circuit. Via the integration of an electronic circuit, for example, a PCB, in and/or on the aid, the generally inflexible electronic circuit can, for example, be arranged outside the pressure-loaded region of the body so that no pressure is likewise applied to the skin surface by the electronic circuit.

An "electronic circuit" is in particular a combination of electrical and/or electronic components forming a functioning assembly. An electronic circuit is, for example, a printed circuit board or PCB. The electronic circuit has various components, such as, for example, a power supply, microcontroller, data memory, real-time clock, Bluetooth module, multiplexer and similar.

To allow telemedical data acquisition and monitoring, the electronic circuit has a communication module for transmitting data to a control device.

The temperature data can be wirelessly transmitted to a control device via a communication module, for example, a Bluetooth module. Continuous monitoring of predesignated skin positions is thus possible, for example, via a smartphone app. Online visualization and evaluation of the temperature differences in a corresponding skin area can also take place using the smartphone app. In the event of a measured value exceeding the threshold as a sign of a pathological event in the skin, an alarm function can advantageously be activated by the app. This also allows for a clinical and/or a preventive monitoring and an active, continuous control of therapy methods by telemedical data acquisition. Data transfer to a higher-level database is in this case advantageous for telemedical therapy control.

A "communication module" is understood to in particular mean an electronic assembly which accepts and transfers data, for example, to an external device such as a control device. A communication module is in particular a transceiver assembly together with associated control components (microcontroller). The assemblies of the communication module can, for example, be configured as plug-in cards on a PCB. The communication module in particular handles the transmission and receival logs, the encryption, the data management, and the transmit control. A communication module in particular transmits in a wired or a wireless manner. The communication module comprises, for example, a Bluetooth interface, a radio module, an RFID transponder or another transmission device.

A "control device" is in particular a computer, tablet, smartphone or other monitoring device which receives and further processes the data from the communication module. The control device also in particular serves to issue an alarm if a threshold value is exceeded, for self-monitoring by a patient, and for telemedical therapy control and monitoring.

It is particularly advantageous if the electronic circuit has an activation sensor, such as, for example, a six-axis acceleration sensor, on the rigid PCB. In the event of a movement, the temperature sensors are activated by way of the acceleration sensor and, as a result, enter a measuring mode. The temperature sensors thus do not measure continuously, but only when the aid is moved and/or worn. This reduces the energy demand and allows for programmable actions in the event of acceleration patterns. Where the aid is an insole, for example, the communication module sends data automatically when the acceleration sensor detects that the insole is turned upside down and the measurements with the insole are therefore finished.

The present invention further provides an aid for application to a skin surface, wherein the aid comprises a sensor layer as described above.

It is thereby reproducibly and repeatably possible for the sensor layer to be applied optimally to a skin surface via the aid. The optimum aid above allows a temperature profile of the corresponding skin surface to be detected via the connected sensor layer and to be selected according to the position of the relevant skin surface.

An aid has already been defined herein. The aid can, for example, be an object that is applied directly on to and/or around a body part, for example, a bandage, or around an object on which a person sits or lies, such as the seat surface of a wheelchair or the sheet in a care bed.

The present invention also provides a method for producing an aid, wherein the aid can be applied to a skin surface, the method comprising the following steps:

Depositing conductor tracks on a top side of the at least one ply and/or into the at least one ply;

Arranging a plurality of temperature sensors in the at least one ply and/or on the top side of the at least one ply and connecting each temperature sensor between two conductor tracks;

Depositing a contact layer on the top side of the at least one ply with the temperature sensors so that a sensor layer is formed; and Depositing a bottom side of the at least one ply on an aid preform or on an aid and/or shaping the aid preform with the connected sensor layer so that an aid is present.

To produce a shoe insole with a sensor layer as an aid, conductor tracks can, for example, first be introduced into the ply. A plurality of temperature sensors corresponding to the skin region of the foot to be monitored are then arranged in the ply so that each temperature sensor borders the top side of the ply, each temperature sensor being stuck or soldered between two conductor tracks. The ply with the conductor tracks and the temperature sensors is then stuck with its bottom side onto an insole preform as a prefabricated sensor layer. A cushion layer is stuck as a contact layer on the top side of the ply where the temperature sensors are arranged. The insole blank with the embedded sensor layer is then shaped by cutting, stamping and/or grinding off excess material.

In the event that the sensor layer has a bottom ply and a top ply, the following steps can be performed:

Depositing conductor tracks on to a top side of a bottom ply;

Laying a top ply onto the bottom ply with the conductor tracks;

Arranging a plurality of temperature sensors on a top side of the top ply and/or in the top ply and connecting each temperature sensor between two conductor tracks;

Depositing a contact layer on to the top side of the top ply with the temperature sensors so that a sensor layer is formed; and Depositing the bottom side of the bottom ply on to an aid preform or on to an aid and/or shaping the aid preform with the connected sensor layer so that an aid is present.

The present invention also provides a method for determining a relative temperature difference on a surface, wherein a sensor layer as described above or an aid as described above is used, having the following steps:

Fitting the sensor layer to the skin surface so that the contact layer of the sensor layer is in contact with the skin surface or with a textile surface surrounding the skin surface;

Measuring temperatures via the plurality of temperature sensors in the sensor layer; and Determining a temperature difference between the plurality of temperature sensors so that an inflammation of the skin surface is identifiable at an early stage based on a local temperature increase.

A method for determining a relative temperature difference and for the early identification of tissue defects on the skin surface is thereby provided. It is particularly advantageous that, via the method according to the present invention, a continuous and even a long-term monitoring of the skin surface is made possible without resulting in the occurrence of a pressure load on the skin, and thus a deterioration of tissue defects, due to the measuring sensor system.

After temperatures have been measured by the plurality of temperature sensors, the measured values recorded can, for example, each be compared with measured values of neighboring temperature sensors and/or with measured values recorded earlier.

Where two aids are used in parallel, for example, a right and a left insole, the measured values of the one aid are compared with the measured values of the other complementary aid. The values determined from different aids can in this case be linked via a communication module, wherein the communication module can in particular receive data as soon as one of the aids signals operational readiness to the communication module.

At least two calibrations or a plurality of calibrations are thus advantageously performed, wherein the calibrations each relate to current recorded measured values from the same and/or a complementary sensor layer and/or were recorded in the past. At least two calibrations can, for example, be performed before a temperature difference is output as harmful.

In an additional step of the method, a control of the measuring is performed via a six-axis acceleration sensor. The acceleration sensor activates the temperature sensors, thereby putting them into measuring mode. The temperature sensors consequently only measure when the aid is being used and/or worn. The energy demand of the sensor layer and/or of the aid is thereby minimized.

Other programmable actions, such as, for example, the initiation of a data transfer, can be predefined in the event of acceleration patterns.

The present invention will be explained in greater detail below with the aid of exemplary embodiments as shown in the drawings.

A sensor layer 101 has a PU bottom ply 107 and a PU top ply 105. Conductor tracks 109 are arranged between the PU bottom ply 107 and the PU top ply 105. The conductor tracks 109 are distributed conformably and in a vein-like and meandering manner over a surface of the PU bottom ply 107 and are guided out at the side between the PU bottom ply 107 and the PU top ply 105 as an electrical connection 119 for the electrical bonding of a PCB 113, which is arranged in the aid preform 115.

A plurality of temperature sensors 111 are arranged on the PU top ply 105. Each temperature sensor 111 is connected between two conductor tracks 109 via an electrical connection 119. The temperature sensors 111 each have a height of 1.5 mm (which is not shown to scale in FIG. 1) and a measuring radius of 2.0 cm. A cushion layer 117 with a contact surface 103 is glued on to the top side of the PU top ply 105 with the temperature sensors 111.

The sensor layer 101 with the cushion layer 117 and with the aid preform 115 glued on the bottom is cut to size and used as a pad in a knee bandage. The knee bandage is applied to a patient's newly operated knee, wherein, because of the PU plies 105, 107 and the flexible, meandering conductor tracks 109, the sensor layer 101 can be optimally fitted to the knee without applying pressure to the newly operated knee. The contact surface 103 is thus in direct contact with the skin surface of the knee.

The current temperature is measured continuously by the temperature sensors 111 and transmitted to a central control device (not illustrated) via Bluetooth by way of the PCB 113. In the control device, the temperature differences between the individual temperature sensors 111 are determined and stored. An alarm is triggered if over 36 hours an increasing rise in a local temperature is detected in one of the temperature sensors 111 and a stipulated threshold value is thereby exceeded. During a medical check-up, an inflammation is accordingly identified at the surgical suture relating to the position of the one temperature sensor 111 and is thereupon treated promptly by a doctor without the occurrence of sequelae.

In an alternative, a sensor layer (not shown) has a single-ply PU layer (not shown). The conductor tracks 109 and the temperature sensors 111 are embedded in this PU layer, the top side of the temperature sensors 111 being flush with the top side of the PU layer. Each temperature sensor 111 is electrically connected between two conductor tracks 109. A cushion layer 117 with a contact surface 103 is stuck onto the top side of the single-ply PU layer with the temperature sensors 111. With its bottom side, the single-ply PU layer is stuck on an aid preform 115. The temperature measurements with this alternative sensor layer accordingly take place as described above.

The present invention is not limited to embodiments described herein; reference should be had to the appended claims.

LIST OF REFERENCE NUMERALS

101 Sensor layer
103 Contact surface
105 PU top ply
107 PU bottom ply
109 Conductor tracks
111 Temperature sensor
113 PCB
115 Aid preform
117 Cushion layer
119 Electrical connection

What is claimed is:

1. A sensor layer for determining temperature profiles on a skin surface, the sensor layer comprising:

at least one ply comprising a bottom ply and a top ply, the top ply comprising a top side;

a contact layer which is configured to contact the skin surface, the contact layer being arranged on the top side of the top ply;

a plurality of temperature sensors arranged on the top side of the top ply; and conductor tracks arranged at least one of in the at least one ply and on a top side of the bottom ply, the conductor tracks being electrically connected to the plurality of temperature sensors so that the sensor layer is formed to be flexible and so that a temperature difference on the skin surface can be determined via the contact layer.

2. The sensor layer as recited in claim 1, wherein, the conductor tracks are arranged between the bottom ply and the top ply, and the conductor tracks are electrically connected to the plurality of temperature sensors on the top side of the top ply.

3. The sensor layer as recited in claim 2, wherein, the at least one ply further comprises a bottom side, and the sensor layer is connected to an aid via the bottom side of the at least one ply or via the bottom ply.

4. The sensor layer as recited in claim 3, further comprising:

an electronic circuit, wherein, the conductor tracks are electrically connected to the electronic circuit at least one of in and on the aid.

5. The sensor layer as recited in claim 4, wherein the electronic circuit is a PCB.

6. The sensor layer as recited in claim 4, further comprising:

a control device, wherein, the electronic circuit comprises a communication module which is configured to transmit data to the control device.

7. The sensor layer as recited in claim 1, wherein the conductor tracks are formed so as to be at least one of evenly spaced, meandering, and vein-like.

8. The sensor layer as recited in claim 1, wherein the sensor layer further comprises a flexible plastic.

9. The sensor layer as recited in claim 8, wherein the flexible plastic is polyurethane.

10. The sensor layer as recited in claim 1, wherein each of the plurality of temperature sensors has a maximum dimension of ≤2 mm.

11. The sensor layer as recited in claim 1, wherein each of the plurality of temperature sensors has a measuring radius of from 1.5 cm to 2.5 cm.

12. The sensor layer as recited in claim 1, wherein the contact layer is provided to be thermally insulating so that a brief temperature increase on the skin surface is determined in an attenuated manner.

13. An aid for application to a skin surface, the aid comprising the sensor layer as recited in claim 1.

14. A method for determining a relative temperature difference on a skin surface using the aid as recited in claim 13, the method comprising:

fitting the sensor layer to the skin surface so that the contact layer of the sensor layer is in contact with the skin surface or with a textile surface surrounding the skin surface;

measuring temperatures via the plurality of temperature sensors in the sensor layer; and determining a temperature difference between the plurality of temperature sensors so that an inflammation of the skin surface is identifiable at an early stage on the basis of a local temperature increase.

* * * * *